(12) United States Patent
Turdjian

(10) Patent No.: US 8,161,975 B2
(45) Date of Patent: Apr. 24, 2012

(54) DUAL MODE IMPULSE NOISE PROTECTING EARPLUG (D-182)

(75) Inventor: Crest Turdjian, Los Angeles, CA (US)

(73) Assignee: Moldex-Metric, Inc., Culver City, CA (US)

( * ) Notice: Subject to any disclaimer, the term of this patent is extended or adjusted under 35 U.S.C. 154(b) by 317 days.

(21) Appl. No.: 12/454,678

(22) Filed: May 21, 2009

(65) Prior Publication Data

US 2010/0294285 A1 Nov. 25, 2010

(51) Int. Cl.
*A61F 11/06* (2006.01)
*A61F 11/00* (2006.01)
*A61B 7/02* (2006.01)
*H02B 1/00* (2006.01)

(52) U.S. Cl. ......... 128/867; 128/864; 181/135; 381/123

(58) Field of Classification Search .................. 181/135, 181/130, 134, 129, 294; D24/106, 174; D29/112; 2/209, 918, 68; 381/324, 123, 72; 128/864, 128/865, 867

See application file for complete search history.

(56) References Cited

U.S. PATENT DOCUMENTS 6,148,821 A * 11/2000 Falco ............................ 128/864

* cited by examiner

*Primary Examiner* — Patricia Bianco
*Assistant Examiner* — Ophelia Hawthorne
(74) *Attorney, Agent, or Firm* — Charles H. Schwartz

(57) ABSTRACT

A two piece dual mode earplug including an integrally molded elongated member having a nose end and an open rear end and a channel extending through. An integrally molded insert member is formed with a base portion and a rod portion and with the rod portion seated within the open rear end of the elongated member and includes an attenuation filter integrally molded as part of the rod portion and includes first and second openings located on each side of a chamber and with the size and length of the openings together with the chamber providing attenuation of impulse noise. The insert member also includes the base portion integrally molded to have a third opening larger than the first and second openings in the rod portion and with the first, second and third openings together forming a passageway through the insert member to the channel extending through the elongated member.

20 Claims, 2 Drawing Sheets

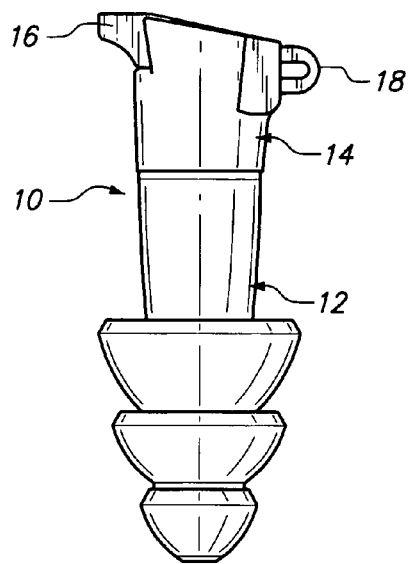
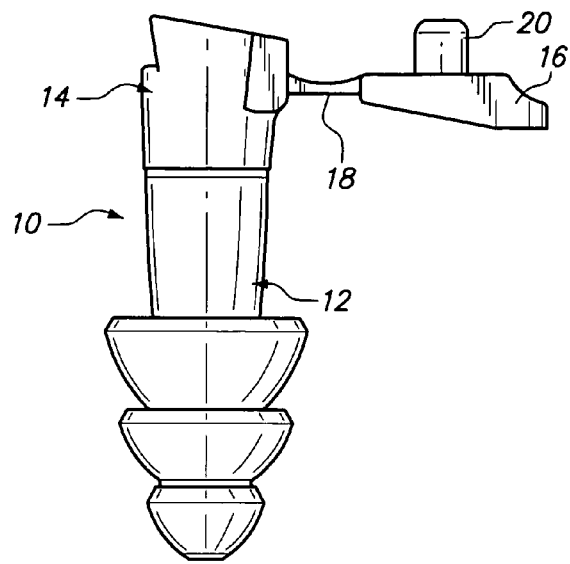
FIG. 1      FIG. 2
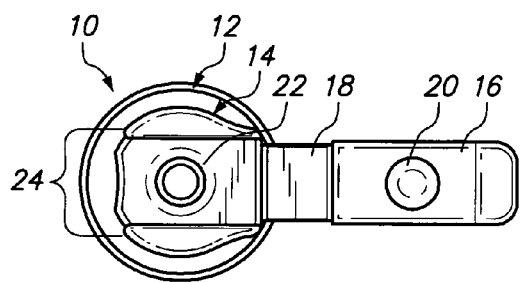
FIG. 3
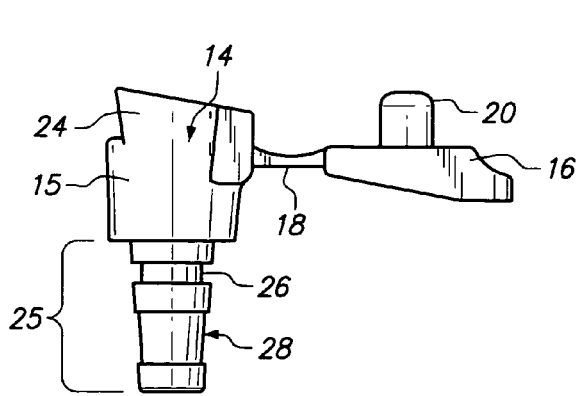
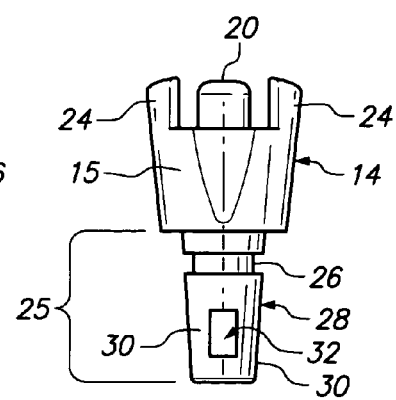
FIG. 4      FIG. 5

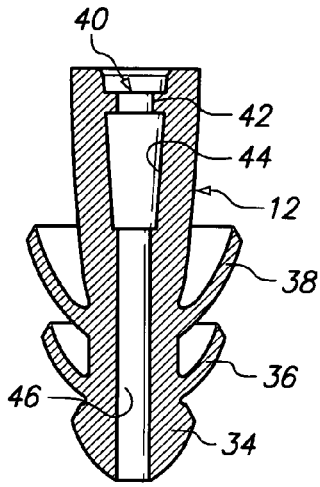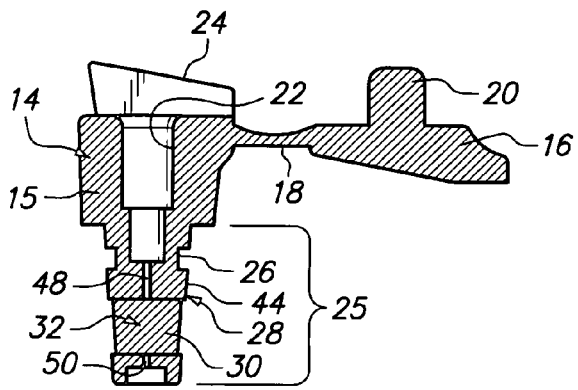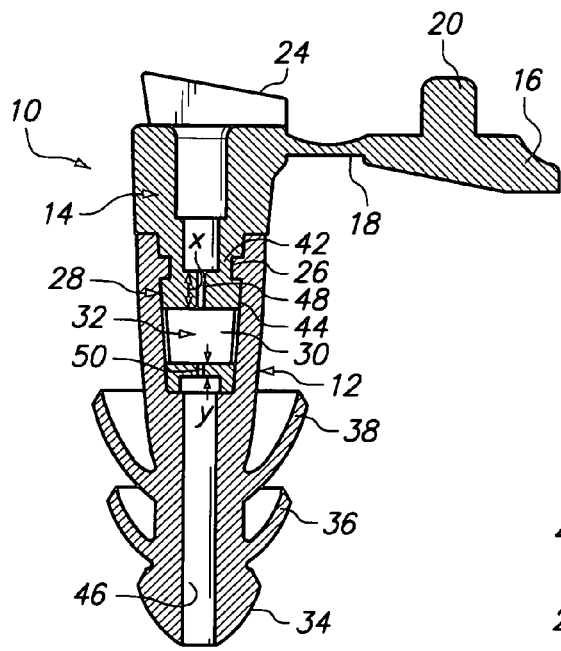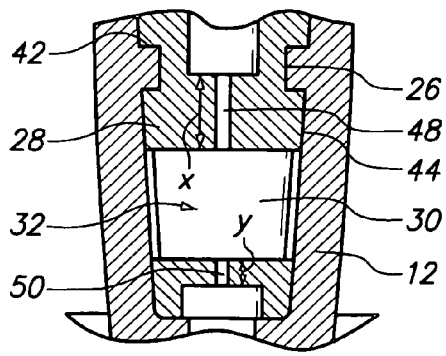

DUAL MODE IMPULSE NOISE PROTECTING EARPLUG (D-182)

BACKGROUND OF THE INVENTION

1. Field of the Invention

This invention relates to a hearing protective earplug for controlling communication between the eardrum and the outside of the ear. In particular, the invention is specifically directed to a hearing protective earplug having selective attenuating characteristics to protect against impulse noise while allowing normal conversation in one mode of operation, and in the second mode of operation providing for high attenuation of all sounds between the outside of the ear and the eardrum.

2. Prior Art

The external sounds directed to the eardrum are generally comprised of a mixture of different sound wave frequencies and different intensities of these sound wave frequencies. It is desirable to control the exposure of the ear to waves of high sound pressure level intensities so as to prevent any temporary or permanent hearing loss. For example, sound of varying frequencies can have high intensity to thereby ultimately provide damage to the auditory organ and can cause serious hearing problems including hearing loss and even deafness. Various occupations can be subjected to these high intensity noises such as constructor workers, individuals who operate heavy or noisy equipment and those in the military during explosions or the operation of military weapons. At the same time it is often desirable that individuals be able to communicate while at the same time guard against any of these high intensity noises. At other times it may be desirable to completely shut off, as much as possible, any outside sounds if they are continuing on a constant basis.

There have been prior art earplugs that have attempted to provide against these loud impulse noises while at the same time allowing normal conversation and providing for the selective control of the earplug from a position of complete blocking of the ear canal to a more selective blocking of the ear canal. One such patent is Falco U.S. Pat. No. 6,148,821 which illustrates an earplug including a separate impulse noise filter member and a rotatable structure for either completely closing off the earplug or for allowing the earplug to allow normal communication while at the same time blocking high impulse noise. The structure of this patent is somewhat complex including numerous parts to achieve the two modes of operation. Another prior art patent that includes this combination of features is Woods U.S. Pat. No. 4,353,364 which encompasses a plug member that can be transferred from one storage opening to another active opening to provide for the selective attenuation in the different modes of operation. This patent also includes a number of individual pieces that together form the structure of the earplug.

There are other patents which operate to provide for the above two modes of operation by using a double-ended plug. One end of the plug is used for complete blocking of sound and the other end of the plug is used for selective blocking of external sounds. This structure can be seen in Hamery U.S. Pat. Nos. 5,936,208 and 6,070,693. The earplug must be removed from the ear canal to go between the two modes of operation In addition to the above, there are prior art patents that include some but not all of the features of the present invention. For example, the Knight U.S. Pat. No. 2,717,596 and de Boer U.S. Pat. No. 4,587,965 provide for earplugs having selective attenuation but do not provide for the plug being completely obscured to prevent the maximum reduction in sound passing to the ear canal. On the other hand, Hocks et al U.S. Pat. No. 281,759 does provide for a plug that can be opened or closed to control the passage or non-passage of sounds to the ear canal but does not provide for the kind of dual mode selective attenuation that is present in the ear protector of the present invention.

There are presently on the market a number of earplugs that include a central shaft and extending therefrom at a nose end that may include at least a single flange. The earplugs are generally composed of a resilient elastomeric material such as synthetic rubber material. The flange element extends outwardly from the nose end of the shaft member and also extends rearwardly from the nose end and is so spaced so as to provide a free annular space between the flange and the shaft. One basic earplug of this type is generally referred to as the V-51R earplug and was developed during the course of World War II in order to provide improved hearing protection to members of the military who were subjected to excessive sound.

In use, this type of earplug is forcibly inserted into the ear canal, thereby at least partially collapsing the rearwardly extending flange element into the underlying free annular space and conforming the flange element into an acoustic sealing relationship with the walls of the ear canal.

SUMMARY OF THE INVENTION

The present invention achieves all of the dual mode advantages of the prior art and eliminates the deficiencies. In particular, the present invention is simple in construction, simple in manufacture, and simple in use. It consists of only two parts which can molded individually and joined together in a simple manufacturing operation. The result is the protective earplug of the present invention that has two modes of operation. For the first mode of operation the earplug provides selective attenuation to allow the passage of normal communications while blocking any high intensity or impulse noise sufficiently to prevent damage to the ear canal. In the second mode of operation, the ear canal is blocked completely to provide high attenuation to all sounds including communication and any high intensity noises. The present invention is easy to use since the switching between the two modes of operation is accomplished using one hand and without removing the earplug from the ear canal. Another feature of the present invention is that it is easy to determine which mode the earplug is in as opposed to some of the prior art where it is sometimes difficult to know which mode has been engaged.

The earplug of the present invention is constructed of front elongated member and a rear insert member. The insert member, located at the rear, forms part of the shaft of the earplug. This rear insert member is made of a relatively hard polymeric material. The other front elongated member forming the earplug is made of a relatively soft resilient material so as to be comfortable within the interior of the ear.

The earplug of the present invention is thereby formed by a shaft composed of the two members and with at least the single elongated member extending from the shaft and having a nose end configuration. The nose end has a rounded cone shape so as to be easily inserted within the ear.

A clearer understanding of the invention will be had with reference to the following description and drawings wherein

BRIEF DESCRIPTION OF THE DRAWINGS

FIG. 1 is a side view of the earplug of the present invention in a closed position for high-level noise protection, FIG. 2 is a side view of the earplug of the present invention in the open position for high impulse noise protection while permitting transmission of low level sounds, FIG. 3 is a top view of the earplug in the open position, FIG. 4 is a side view of an insert member of the earplug in the open position, FIG. 5 is a front view of the insert member of the earplug in the open position, FIG. 6 is a cross-sectional view of an elongated member of the earplug, FIG. 7 is a cross-sectional view of the insert portion of the earplug, FIG. 8 is a cross-sectional view of the earplug with the insert portion inserted into the elongated member and with the earplug in the open position, and FIG. 8(a) is an expanded portion of FIG. 8.

DETAILED DESCRIPTION OF THE INVENTION

As shown in FIGS. 1 and 2, the earplug 10 of the present invention includes an elongated member 12 forming a nosepiece and an insert member 14. In addition, the insert member 14 includes a living hinged cap member 16 attached to the body of the insert portion 14 by the living hinge 18. The cap member 16 includes a plug 20 that is used to switch the mode of operation by the insert member 14 from the closed position of FIG. 1 to the open position of FIG. 2.

This can be seen more clearly in the top view of FIG. 3 where it is seen that the insert member 14 includes an opening 22 and when the cap member 16 is in the closed position of FIG. 1, the plug 20 enters into the opening 22 to completely close off the opening 22. This blocks the earplug 10 from transmission of any sound energy through the earplug. The insert member 14 includes a base portion 15 with a pair of sidewalls 24 so that the cap member 16 is guided in between the sidewalls 24 to ensure that the plug 20 is properly seated within the opening 22.

FIG. 4 illustrates the insert member 14 having a lower rod portion 25 extending downward and including a locking portion 26 and a high impulse noise filter portion 28. A front view of the insert 14 member is shown in FIG. 5 illustrating the insert member 14 and specifically the lower rod portion includes the locking portion 26 and the impulse noise filter portion 28. The impulse filter portion 28 includes a pair of side walls 30 and a chamber opening 32 which extends through the lower rod portion of the insert member 14.

FIG. 6 illustrates a cross-sectional view of the elongated member 12 of the ear protector of the present invention. In particular, the elongated member is shown to include a bulbous nose member 34 and a pair of flange members 36 and 38. This elongated member 12 is shown to be a type shown in prior U.S. Pat. No. 5,957,136. It is to be appreciated that the elongated member 12 can take any shape either including flanges or not including flanges and can be made of various types of material such as the type of material disclosed in U.S. Pat. No. 5,957,136 or other materials including rubber-like materials or foam materials. The external shape of the elongated member 12 is preferred but other shapes can be used as long as the internal structure of the elongated member is part of the ear protector of the present invention.

In particular the internal structure of the elongated member 12 includes a channel 40 that extends completely therethrough. The channel 40 is formed with a portion 42 that interacts with the locking portion 26 of the insert member 14 to seat and mechanically lock the insert in position within elongated member 12. The channel 40 further includes a chamber portion 44 that cooperates with the high impulse noise filter portion 28 of the insert 14 to provide for the attenuation of high impulse noise. The channel 40 further includes a passage 46, which leads into the ear canal of the wearer of the earplug.

The combination of an elongated member 12 made of material softer than the material of the insert member 12 also allows for the advantages of the insert member in forming a handle for insertion of the earplug in the ear canal. The earplug of the present invention can be fabricated by any suitable polymer molding techniques. It is important that the earplug be constructed of the proper resilient polymer material so as to have the combination of softness at the end of the earplug that is inserted into the ear and hardness at the rearward end to facilitate the insertion.

For example the elongated member 12 should be formulated of material that have a Shore A Durometer hardness value (by the technique of ASTM 2240-81) of between about 10 and 30 and preferably between 15 and 25. The insert member 14 should be composed of a resilient polymeric material having a higher Shore A Durometer hardness value between 50 and 120 and preferably between 70 and 90. In a preferred embodiment the elongated member 12 can have a Shore A Durometer hardness value of approximately 20 and the insert member 14 can have a Shore A Durometer hardness value of approximately 85.

FIG. 7 is a cross-sectional view of the insert member 14 and shows the opening 22 to receive the plug 20 so that the ear protector may be switched from the open-to-close positions by positioning the cap member 16 using the living hinge 18. The insert member 14 is also shown to have the locking portion 26 that cooperates with the locking portion 42 of the elongated member 12 for seating and locking the insert member within the elongated member 12.

The impulse noise filter also includes a first opening 48 that extends from the opening 22 into the chamber area 32. A second opening 50 extends out of the chamber area 32 into the opening 46 of the elongated member 12. It is the combination of the size of the openings 48 and 50 and lengths x and y (shown in FIG. 8(a)) of the openings together with the chamber portion 32 forming a third larger opening and the adjacent wall portion of the chamber 44 of the elongated member 12 which together form the high impulse noise filter. This type of filter is known and is disclosed in the prior art patents indicated above. These prior art filters have generally been formed by separate elements that are in addition to the structure of the ear protector itself. In the present invention, all of the filtering elements plus the ability to close off the plug completely from the open-to-close modes of operation is accomplished using just two molded members, the insert member 14 and elongated member 12.

There are many known resilient polymeric materials that may be used to form the earplugs of the present invention. For example, natural rubber, neoprene rubber, SBR rubber (styrene block copolymer compounds), silicone rubber, EPDM rubber, polybutadiene rubber, polyvinylchloride elastomers and foams. polyurethane elastomers and foams, ethylene vinyls, acetate elastomers, elastomers based on acrylic acid precursors and vinyhalide polymers may all be generally suitable materials which can be used to provide the necessary Shore A Durometer values. As preferred materials the present invention contemplates using a polyvinylchloride elastomer with low migration for the member 14 and SBR rubber for the elongated member 12.

The final combined structure can be seen in FIG. 8 wherein the insert member 14 has been inserted into the elongated member 12 and where all of the various members are shown cooperating to provide for the operation of the present invention. As shown in FIG. 8, the earplug 10 is in the open position. In this mode of operation external sounds can enter into the opening 22 to be passed into the interior of the earplug. Various sound frequencies and intensities of sounds then have to pass through the small opening 48 and then into the chamber 32 formed by the sidewall 30 and also the side portions of the elongated member 12. Sounds entering into chamber 32 may then pass through opening 50 and thereby into the passageway 46 to the interior of the ear. The combination of the size of the openings 48 and 50, the length of the opening x and y, shown in FIGS. 8 and 8(a), and the size of the chamber 32 form the high intensity filter to attenuate high intensity or impulse noise. Meanwhile normal conversation can be heard but in somewhat attenuated form.

When the plug 20 engages into the opening 22 and thereby completely shuts off the earplug, then all external noise is blocked to the passageway 46. All of this is accomplished using the two parts 12 and 14 that may be easily molded using conventional equipment. Moreover, the two parts are interlocked in a very simple manner using the interlocking portions 26 and 42 and it is only necessary to insert the insert into the plug portion, push it in until these two portions 26 and 42 interlocked to hold the earplug in the completed assembled position. It is also noted that the bottom portion 28 of the insert 14 is tapered as is the passageway 44 of the elongated member and this also helps in the assembly since it is easier to assemble using these tapered portions.

In general, the operation of the earplug 10 by a user is a follows:

When cap 16 is open, the earplug 10 can be used to reduce impulse noises, such as gunfire, while also allowing the user to hear low-level noise. In the closed cap position the earplug can be used to help protect against continuous and impulse noises.

For use against continuous noise, insert, as below, and wear with the cap 16 closed. Before inserting the earplug 10, check to see that cap 16 is fully closed shut. Reach over the head and pull top of ear upwards. With the other hand grasp insert member 14 and gently push and wiggle into the ear canal until a good and comfortable seal is made.

For use against impulse noise when low level hearing is needed, wear with the cap 16 open and insert as above. If the earplug is already being worn with cap 16 closed, there is no need to take the plug out to open cap. To open the cap 16, depending on the orientation of the insert member 14, use either the thumb or index finger to gently push out on the cap 16 while resting the other finger on the hinge 18. If you want to switch to use against continuous noise the cap must be closed. To close cap 16 there is no need to take earplug out. Depending on the orientation of the insert member 14, use either the thumb or index finger to gently push the cap 16 in the insert member 14.

It can therefore seem that all of the desirable features of the dual mode operation have been accomplished in the present invention. Moreover, the method and structure of switching between the open and closed positions for the two difference modes of operation is very simply accomplished using the plug member 20 which engages an opening 22 and that is part of the insert member 14 using a living hinge 18. It is very simple to reach up and with one hand to switch the earplug from the closed position to the open positioned and then to re-engage the closed position by just pushing the cap portion 16 to have the plug engage the opening. This structure is much simpler than any other prior art that either require a rotational movement or with the removal of an actual plug member and transferring it from one position to another.

The present invention has simplicity of manufacture using only two parts and simplicity of the structure itself. Both parts may be easily molded using conventional techniques and the present invention has simplicity of assembly by merely pushing one member into the other to assemble the complete earplug. All of this greatly simplifies the structure and manufacturing when compared with prior art devices. Moreover, the ease of operation from one mode to the other again increases the advantages of the present invention. The novel and unique combination of elements thereby lends a surprising structural advantage of the present invention over the prior art.

As indicated above, the elongated member may take any form and although the invention has been described with reference to a particular embodiment it is to be appreciated that various adaptations and modifications may be made and the invention is only to be limited by the appended claims.

I claim:

1. A two piece dual mode earplug and with each piece molded of resilient polymeric material for insertion into an ear canal, including:
   a. an integrally molded elongated member having a nose end and an open rear end and a channel extending through the interior of the integrally molded elongated member from the open rear end to the nose end,
   b. an integrally molded insert member formed with a base portion and a rod portion and with the rod portion seated within the open rear end of the integrally molded elongated member and extending into the channel of the elongated member and with the base portion extending out from the open rear end of the elongated member and serving as a handle for aiding insertion of the earplug into an ear canal,
   c. the integrally molded insert member additionally including an attenuation filter integrally molded as part of the rod portion and including first and second openings located on each side of a chamber and with the size and length of the openings together with the chamber providing attenuation of impulse noise while allowing the passage of normal speech through the channel extending through the interior of the integrally molded elongated member,
   d. the integrally molded insert member also including the base portion integrally molded and including a third opening larger than the first and second openings in the rod portion and with the first, second and third openings together forming a passageway through the insert member to the channel extending through the interior of the integrally molded elongated member,
   e. the integrally molded insert member further including an integrally molded cap member and with the cap member including a plug portion having a size complementary to the third opening of the base member where the insertion of the plug portion into the third opening of the base portion would seal off the third opening and with positioning of the cap member providing for the earplug being in a first mode of operation where the passageway through the insert member to the channel extending through the interior of the elongated member is open and a second mode of operation where the passageway through the insert member to the channel extending through the interior of the integrally molded elongated member is closed, and
   f. the elongated member composed of a resilient polymer material having a relatively low Shore A Durometer hardness value and the insert member composed of a resilient polymeric material having a relatively high Shore A Durometer hardness value so that the insert member forms a handle of greater stiffness to enable the elongated member to be more easily inserted into the ear canal and allows the cap member to be easily switched between the two modes of operation of the earplug with one hand without removing the earplug from the ear canal.

2. The two piece earplug of claim 1 wherein the exterior configuration of the rod portion of the integrally molded insert member is substantially the same as the interior configuration of the open rear end of the elongated member.

3. The two piece earplug of claim 2 wherein the rod portion of the integrally molded insert member and the open rear end of the integrally molded elongated member have complementary interlocking portions to mechanically lock the rod portion of the integrally molded insert member within the open rear end of the integrally molded elongated member when they are seated.

4. The two piece earplug of claim 1 wherein an attenuation chamber is formed partially by the integrally molded insert member and partially by the open rear end of the integrally molded elongated member.

5. The two piece earplug of claim 1 wherein the cap member is attached to the base portion of the insert integrally molded member by an integrally molded hinge member and with the positioning of the cap member provided by moving the cap member using the hinge member.

6. The two piece earplug of claim 1 wherein the integrally molded elongated member includes at least two hollow rearwardly extending flange elements of serially increasing diameters and with the nose end having a smaller diameter than any of the flange elements.

7. The two piece earplug of claim 1 wherein the base portion of the integrally molded insert member is of substantially the same diameter as the rear end of the integrally molded elongated member to form a smooth shaft portion rearward of the integrally molded elongated member.

8. The two piece earplug of claim 1 wherein the rod portion is mechanically seated within the open rear end of the integrally molded elongated member.

9. The two piece earplug of claim 1 wherein the integrally molded elongated member is composed of a resilient polymeric material having a Shore A Durometer hardness value of between 10 and 30 and the integrally molded insert member is composed of a resilient polymeric material having a Shore A Durometer hardness value of between 50 and 120.

10. The two piece earplug of claim 1 wherein the integrally molded elongated member has a Shore A Durometer hardness value of between 15 and 25 and the integrally molded insert member has a Shore A Durometer hardness value of between 80 and 90.

11. A two piece dual mode earplug and with each piece molded of resilient polymeric material for insertion into an ear canal, including:
   a. an integrally molded elongated member having a nose end and an open rear end and a channel extending through the interior of the elongated member from the open rear end to the nose end,
   b. an integrally molded insert member formed with a base portion and a rod portion and with the rod portion seated within the open rear end of the integrally molded elongated member and extending into the channel of the integrally molded elongated member,
   c. the integrally molded insert member additionally including an attenuation filter integrally molded as part of the rod portion and including first and second openings located on each side of a chamber and with the size and length of the openings together with the chamber providing attenuation of impulse noise while allowing the passage of normal speech through the channel extending through the interior of the integrally molded elongated member,
   d. the integrally molded insert member also including the base portion integrally molded and including a third opening larger than the first and second openings in the rod portion and with the first, second and third openings together forming a passageway through the integrally molded insert member to the channel extending through the interior of the integrally molded elongated member, and
   e. the integrally molded insert member further including an integrally molded cap member and with the cap member including a plug portion having a size complementary to the third opening of the base member where the insertion of the plug portion into the third opening of the base portion would seal off the third opening and with positioning of the cap member providing for the earplug being in a first mode of operation where the passageway through the integrally molded insert member to the channel extending through the interior of the elongated member is open and a second mode of operation where the passageway through the integrally molded insert member to the channel extending through the interior of the integrally molded elongated member is closed.

12. The two piece earplug of claim 11 wherein the exterior configuration of the rod portion of the integrally molded insert member is substantially the same as the interior configuration of the open rear end of the integrally molded elongated member.

13. The two piece earplug of claim 12 wherein the rod portion of the integrally molded insert member and the open rear end of the integrally molded elongated member have complementary interlocking portions to mechanically lock the rod portion of the integrally molded insert member within the open rear end of the integrally molded elongated member when they are seated.

14. The two piece earplug of claim 11 wherein an attenuation chamber is formed partially by the integrally molded insert member and partially by the open rear end of the integrally molded elongated member.

15. The two piece earplug of claim 11 wherein the cap member is attached to the base portion of the integrally molded insert member by an integrally molded hinge member and with the positioning of the cap member provided by moving the cap member using the integrally molded hinge member.

16. The two piece earplug of claim 11 wherein the integrally molded elongated member includes at least two hollow rearwardly extending flange elements of serially increasing diameters and with the nose end having a smaller diameter than any of the flange elements.

17. The two piece earplug of claim 11 wherein the base portion of the integrally molded insert member is of substantially the same diameter as the rear end of the integrally molded elongated member to form a smooth shaft portion rearward of the integrally molded elongated member.

18. The two piece earplug of claim 11 wherein the rod portion is mechanically seated within the open rear end of the integrally molded elongated member.

19. The two piece earplug of claim 11 wherein the integrally molded elongated member is composed of a resilient polymeric material having a Shore A Durometer hardness value of between 10 and 30 and the integrally molded insert member is composed of a resilient polymeric material having a Shore A Durometer hardness value of between 50 and 120.

20. The two piece earplug of claim 11 wherein the integrally molded elongated member has a Shore A Durometer hardness value of between 15 and 25 and the integrally molded insert member has a Shore A Durometer hardness value of between 80 and 90.

* * * * *